United States Patent
Hawkins et al.

(10) Patent No.: US 8,956,374 B2
(45) Date of Patent: *Feb. 17, 2015

(54) SHOCKWAVE BALLOON CATHETER SYSTEM

(75) Inventors: Daniel Hawkins, Bellevue, WA (US); Clifton A. Alferness, Port Orchard, WA (US); John M. Adams, Snohomish, WA (US)

(73) Assignee: Shockwave Medical, Inc., Fremont, CA (US)

(*) Notice: Subject to any disclaimer, the term of this patent is extended or adjusted under 35 U.S.C. 154(b) by 385 days.

This patent is subject to a terminal disclaimer.

(21) Appl. No.: 13/049,199

(22) Filed: Mar. 16, 2011

(65) Prior Publication Data

US 2011/0166570 A1 Jul. 7, 2011

Related U.S. Application Data

(62) Division of application No. 12/482,995, filed on Jun. 11, 2009.

(60) Provisional application No. 61/061,170, filed on Jun. 13, 2008.

(51) Int. Cl.
*A61B 17/22* (2006.01)
*A61B 17/225* (2006.01)
*A61B 17/3207* (2006.01)

(52) U.S. Cl.
CPC ....... *A61B 17/2202* (2013.01); *A61B 17/22022* (2013.01); *A61B 17/2251* (2013.01);
(Continued)

(58) Field of Classification Search
CPC .............. A61B 17/2202; A61B 17/22012; A61B 17/22022; A61B 17/225; A61B 17/22007; A61B 17/22008; A61M 37/0092; A61M 25/104
USPC ............. 606/48, 50, 127, 128, 159, 167, 169, 606/170, 1–4; 601/2, 4; 604/22
See application file for complete search history.

(56) References Cited

U.S. PATENT DOCUMENTS

| 3,785,382 A | 1/1974 | Schmidt-Kloiber et al. |
| 4,027,674 A | 6/1977 | Tessler et al. |

(Continued)

FOREIGN PATENT DOCUMENTS

| DE | 3038445 A1 | 5/1982 |
| EP | 0442199 A2 | 8/1991 |

(Continued)

OTHER PUBLICATIONS

International Search Report for International Patent Application No. PCT/US2009/047070, dated Jan. 19, 2010.

(Continued)

*Primary Examiner* — Kathleen Holwerda
(74) *Attorney, Agent, or Firm* — Morrison & Foerster LLP

(57) ABSTRACT

A system for breaking obstructions in body lumens includes a catheter including an elongated carrier, a balloon about the carrier in sealed relation thereto, the balloon being arranged to receive a fluid therein that inflates the balloon, and an arc generator including at least one electrode within the balloon that forms a mechanical shock wave within the balloon. The system further includes a power source that provides electrical energy to the arc generator.

8 Claims, 8 Drawing Sheets

(52) U.S. Cl.
CPC ............. *A61B17/320725* (2013.01); *A61B 2017/22024* (2013.01); *A61B 2017/22025* (2013.01); *A61B 17/22029* (2013.01); *A61B 2017/22058* (2013.01); *A61B 2017/22061* (2013.01); *A61B 2017/22062* (2013.01)
USPC ............... 606/159; 606/128; 606/194; 601/4

(56) References Cited

U.S. PATENT DOCUMENTS

| | | | |
|---|---|---|---|
| 4,662,126 A | | 5/1987 | Malcolm |
| 4,685,458 A | * | 8/1987 | Leckrone ........................ 606/7 |
| 4,900,303 A | | 2/1990 | Lemelson |
| 5,009,232 A | * | 4/1991 | Hassler et al. ................ 600/439 |
| 5,057,103 A | | 10/1991 | Davis |
| 5,078,717 A | | 1/1992 | Parins et al. |
| 5,102,402 A | | 4/1992 | Dror et al. |
| 5,103,804 A | | 4/1992 | Abele et al. |
| 5,152,767 A | | 10/1992 | Sypal et al. |
| 5,152,768 A | | 10/1992 | Bhatta |
| 5,176,675 A | | 1/1993 | Watson et al. |
| 5,246,447 A | | 9/1993 | Rosen et al. |
| 5,281,231 A | | 1/1994 | Rosen et al. |
| 5,324,255 A | | 6/1994 | Passafaro et al. |
| 5,336,234 A | | 8/1994 | Vigil et al. |
| 5,368,591 A | * | 11/1994 | Lennox et al. ................. 606/27 |
| 5,395,335 A | * | 3/1995 | Jang ........................ 604/102.02 |
| 5,417,208 A | | 5/1995 | Winkler |
| 5,425,735 A | | 6/1995 | Rosen et al. |
| 5,472,406 A | | 12/1995 | de la Torre et al. |
| 5,582,578 A | | 12/1996 | Zhong et al. |
| 5,603,731 A | | 2/1997 | Whitney |
| 5,609,606 A | | 3/1997 | O'Boyle |
| 5,662,590 A | | 9/1997 | de la Torre et al. |
| 5,893,840 A | | 4/1999 | Hull et al. |
| 5,931,805 A | | 8/1999 | Brisken |
| 6,007,530 A | | 12/1999 | Dornhofer et al. |
| 6,033,371 A | | 3/2000 | Torre et al. |
| 6,083,232 A | | 7/2000 | Cox |
| 6,146,358 A | | 11/2000 | Rowe |
| 6,210,408 B1 | | 4/2001 | Chandrasekaran et al. |
| 6,217,531 B1 | | 4/2001 | Reitmajer |
| 6,277,138 B1 | | 8/2001 | Levinson et al. |
| 6,287,272 B1 | * | 9/2001 | Brisken et al. ................. 604/22 |
| 6,352,535 B1 | | 3/2002 | Lewis et al. |
| 6,367,203 B1 | | 4/2002 | Graham et al. |
| 6,371,971 B1 | | 4/2002 | Tsugita et al. |
| 6,398,792 B1 | | 6/2002 | O'Connor |
| 6,406,486 B1 | | 6/2002 | DeLa Torre et al. |
| 6,514,203 B2 | | 2/2003 | Bukshpan |
| 6,524,251 B2 | * | 2/2003 | Rabiner et al. ................ 600/439 |
| 6,589,253 B1 | | 7/2003 | Cornish et al. |
| 6,607,003 B1 | | 8/2003 | Wilson |
| 6,638,246 B1 | | 10/2003 | Naimark et al. |
| 6,652,547 B2 | * | 11/2003 | Rabiner et al. ................ 606/159 |
| 6,736,784 B1 | * | 5/2004 | Menne et al. .................... 601/2 |
| 6,740,081 B2 | | 5/2004 | Hilal |
| 6,755,821 B1 | * | 6/2004 | Fry .................................. 606/15 |
| 6,939,320 B2 | | 9/2005 | Lennox |
| 6,989,009 B2 | | 1/2006 | Lafontaine |
| 7,066,904 B2 | | 6/2006 | Rosenthal et al. |
| 7,241,295 B2 | | 7/2007 | Maguire |
| 7,569,032 B2 | | 8/2009 | Naimark et al. |
| 8,728,091 B2 | * | 5/2014 | Hakala et al. ................. 606/128 |
| 2001/0044596 A1 | | 11/2001 | Jaafar |
| 2002/0177889 A1 | | 11/2002 | Brisken et al. |
| 2003/0004434 A1 | | 1/2003 | Greco et al. |
| 2003/0176873 A1 | | 9/2003 | Chernenko et al. |
| 2003/0229370 A1 | | 12/2003 | Miller |
| 2004/0044308 A1 | | 3/2004 | Naimark et al. |
| 2004/0097996 A1 | | 5/2004 | Rabiner et al. |
| 2004/0254570 A1 | | 12/2004 | Hadjicostis et al. |
| 2005/0015953 A1 | | 1/2005 | Keidar |
| 2005/0021013 A1 | | 1/2005 | Visuri et al. |
| 2006/0004286 A1 | | 1/2006 | Chang et al. |
| 2006/0184076 A1 | | 8/2006 | Gill et al. |
| 2006/0190022 A1 | | 8/2006 | Beyar et al. |
| 2007/0088380 A1 | | 4/2007 | Hirszowicz et al. |
| 2007/0239082 A1 | * | 10/2007 | Schultheiss et al. ............ 601/4 |
| 2007/0239253 A1 | | 10/2007 | Jagger et al. |
| 2007/0244423 A1 | | 10/2007 | Zumeris et al. |
| 2008/0097251 A1 | | 4/2008 | Babaev |
| 2008/0188913 A1 | | 8/2008 | Stone et al. |
| 2009/0041833 A1 | | 2/2009 | Bettinger et al. |
| 2009/0247945 A1 | | 10/2009 | Levit et al. |
| 2009/0254114 A1 | | 10/2009 | Hirszowics et al. |
| 2009/0312768 A1 | | 12/2009 | Hawkins et al. |
| 2010/0016862 A1 | | 1/2010 | Hawkins et al. |
| 2010/0036294 A1 | * | 2/2010 | Mantell et al. .................... 601/4 |
| 2010/0114020 A1 | | 5/2010 | Hawkins et al. |
| 2010/0114065 A1 | | 5/2010 | Hawkins et al. |
| 2010/0121322 A1 | | 5/2010 | Swanson |
| 2010/0305565 A1 | | 12/2010 | Truckai et al. |
| 2011/0034832 A1 | | 2/2011 | Cioanta et al. |
| 2011/0118634 A1 | | 5/2011 | Golan |
| 2011/0295227 A1 | | 12/2011 | Hawkins et al. |
| 2012/0071889 A1 | | 3/2012 | Mantell et al. |
| 2012/0095461 A1 | | 4/2012 | Herscher et al. |
| 2012/0203255 A1 | | 8/2012 | Hawkins et al. |
| 2012/0221013 A1 | | 8/2012 | Hawkins et al. |
| 2013/0030431 A1 | | 1/2013 | Adams |
| 2013/0030447 A1 | | 1/2013 | Adams |
| 2014/0005576 A1 | | 1/2014 | Adams et al. |
| 2014/0039513 A1 | | 2/2014 | Hakala et al. |
| 2014/0046229 A1 | | 2/2014 | Hawkins et al. |
| 2014/0052145 A1 | | 2/2014 | Adams et al. |
| 2014/0052147 A1 | | 2/2014 | Hakala et al. |
| 2014/0074111 A1 | | 3/2014 | Hakala et al. |
| 2014/0074113 A1 | | 3/2014 | Hakala et al. |

FOREIGN PATENT DOCUMENTS

| | | |
|---|---|---|
| EP | 571306 A1 | 11/1993 |
| JP | 62-275446 A | 11/1987 |
| JP | 6-125915 A | 5/1994 |
| JP | 7-47135 A | 2/1995 |
| JP | 10-99444 A | 4/1998 |
| JP | 2002-538932 A | 11/2002 |
| JP | 2004-81374 A | 3/2004 |
| JP | 2005-95410 A | 4/2005 |
| JP | 2005-515825 A | 6/2005 |
| JP | 2006-516465 A | 7/2006 |
| WO | 2004/069072 A2 | 8/2004 |
| WO | 2006/127158 A2 | 11/2006 |
| WO | 2007/149905 A2 | 12/2007 |
| WO | 2009/121017 A1 | 10/2009 |
| WO | 2009/152352 A2 | 12/2009 |
| WO | 014515 | 2/2010 |
| WO | 2011/143468 A2 | 11/2011 |

OTHER PUBLICATIONS

Final Office Action received for U.S. Appl. No. 12/581,295, mailed on Jun. 5, 2014, 14 pages.
Office Action received for Australian Patent Application No. 2009257368, issued on Apr. 28, 2014, 4 pages.
Office Action received for Australian Patent Application No. 2009257368, issued on Jul. 31, 2013, 4 pages.
Extended European Search Report (Includes Supplementary European Search Report and Search Opinion) received for European Patent Application No. 09763640.1, mailed on Oct. 10, 2013, 5 pages.
Office Action received for Japanese Patent Application No. 2011-513694, mailed on Aug. 27, 2013, 6 pages (3 pages of English Translation and 3 pages of Official copy).
International Preliminary Report on Patentability received for PCT Patent Application No. PCT/US2011/047070, mailed on Feb. 21, 2013, 7 pages.
International Written Opinion received for PCT Patent Application No. PCT/US2011/047070, mailed on May 1, 2012, 5 pages.
International Preliminary Report on Patentability received for PCT Patent Application No. PCT/US2012/023172, mailed on Aug. 15, 2013, 6 pages.

(56) References Cited

OTHER PUBLICATIONS

International Search Report received for PCT Patent Application No. PCT/US2012/023172, mailed on Sep. 28, 2012, 3 pages.
International Search Report and Written Opinion received for PCT Patent Application No. PCT/US2013/031805 mailed on May 20, 2013, 13 pages.
International Search Report and Written Opinion received for PCT Patent Application No. PCT/US2013/039987, mailed on Sep. 23, 2013, 15 pages.
International Search Report and Written Opinion received for PCT Patent Application No. PCT/US2013/048277, mailed on Oct. 2, 2013, 14 pages.
International Search Report and Written Opinion received for PCT Patent Application No. PCT/US2013/055431, mailed on Nov. 12, 2013, 9 pages.
International Search Report and Written Opinion received for PCT Patent Application No. PCT/US2013/059533, mailed on Nov. 7, 2013, 14 pages.
Final Office Action received for U.S. Appl. No. 12/482,995, mailed on Feb. 20, 2014, 11 pages.
Non Final Office Action received for U.S. Appl. No. 12/482,995, mailed on Jul. 12, 2013, 11 pages.
Non-Final Office Action received for U.S. Appl. No. 12/501,619, mailed on Jan. 28, 2014, 10 pages.
Non-Final Office Action received for U.S. Appl. No. 12/581,295, mailed on Mar. 10, 2014, 11 pages.
Final Office Action received for U.S. Appl. No. 13/267,383, mailed on Oct. 25, 2013, 8 pages.
Non-Final Office Action received for U.S. Appl. No. 14/061,554, mailed on Mar. 12, 2014, 14 pages.
Notice of Allowance received for U.S. Appl. No. 14/061,554, mailed on Apr. 25, 2014, 8 pages.
Non Final Office Action received for U. S. Appl. No. 14/079,463, mailed on Mar. 4, 2014, 9 pages.
Notice of Allowance received for U.S. Appl. No. 14/079,463, mailed on Apr. 1, 2014, 5 pages.
Adams et al., Unpublished U.S. Appl. No. 14/271,342, filed May 6, 2014, titled "Shock Wave Balloon Catheter with Multiple Shock Wave Sources", 21 pages.
Adams, John M. ,U.S. Appl. No. 14/218,858, filed Mar. 18, 2014, titled "Shockwave Catheter System with Energy Control", 24 pages.
Adams, John M., Unpublished U.S. Appl. No. 14/273,063, filed May 8, 2014, titled "Shock Wave Guide Wire", 24 pages.
Hakala et al., Unpublished U.S. Appl. No. 14/271,276, filed May 6, 2014, titled "Shockwave Catheter System with Energy Control", 20 pages.
Rosenschein et al., "Shock-Wave Thrombus Ablation, a New Method for Noninvasive Mechanical Thrombolysis", The American Journal of Cardiology, vol. 70, Nov. 15, 1992, pp. 1358-1361.
Zhong et al., "Transient Oscillation of Cavitation Bubbles Near Stone Surface During Electohydraulic Lithotripsy", Journal of Endourology, vol. 11, No. 1, Feb. 1997, pp. 55-61.
Advisory Action received for U.S. Appl. No. 13/267,383, mailed on Jan. 6, 2014, 4 pages.

* cited by examiner

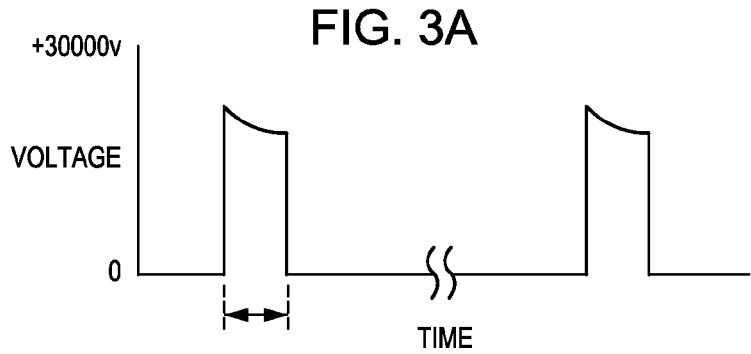
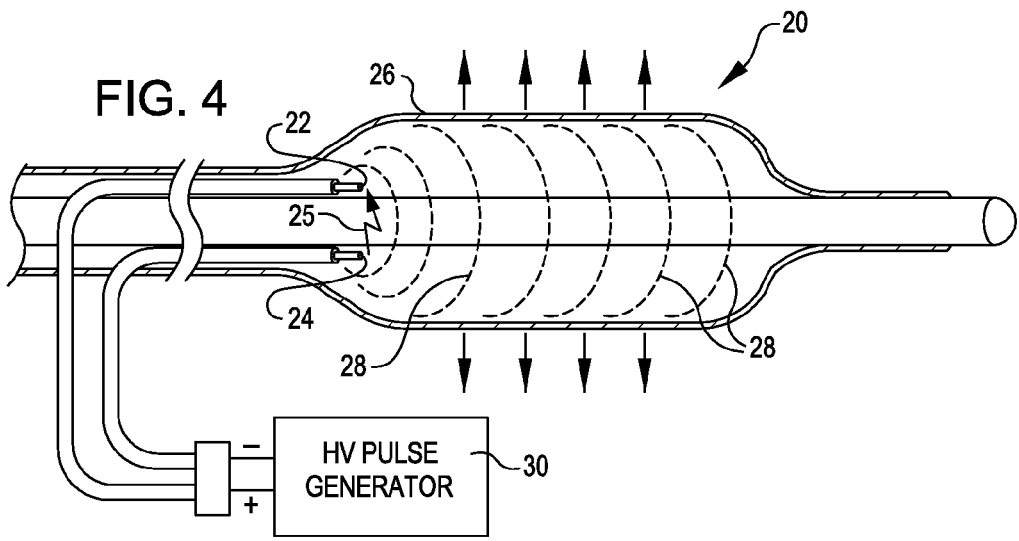
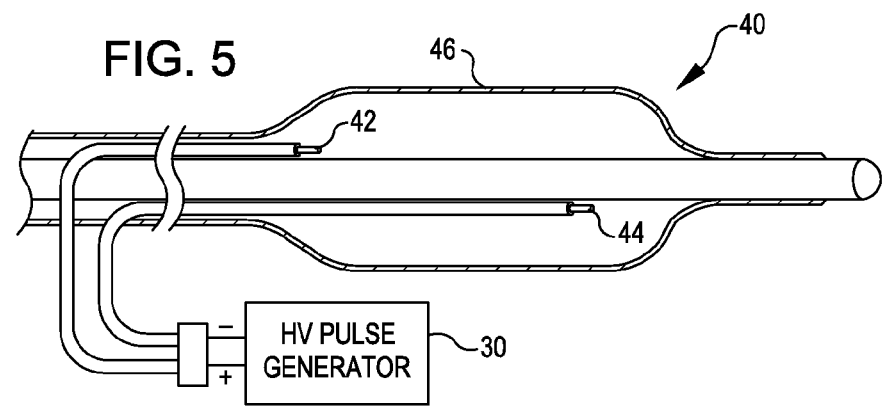

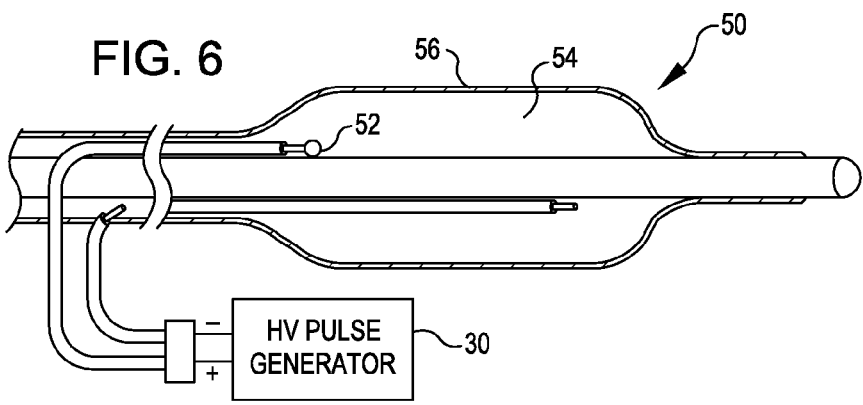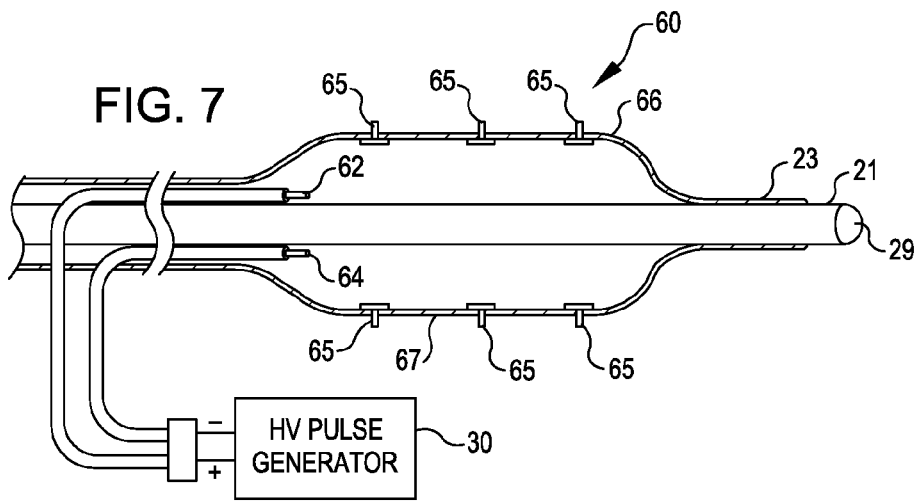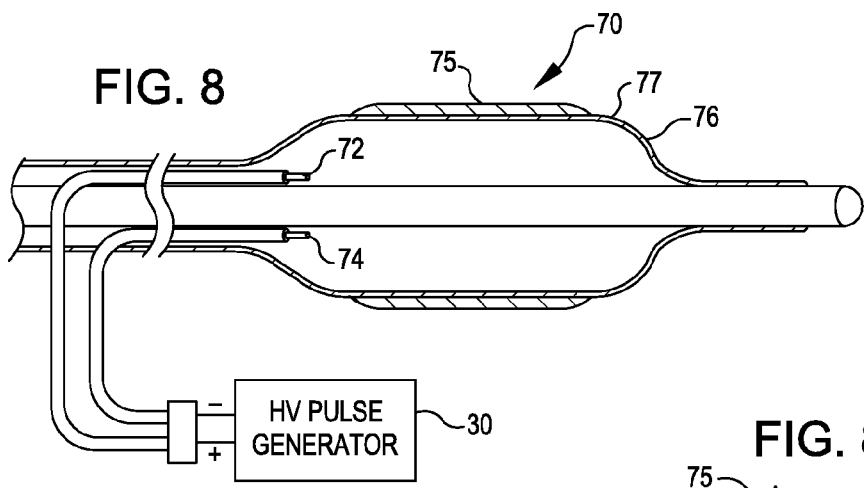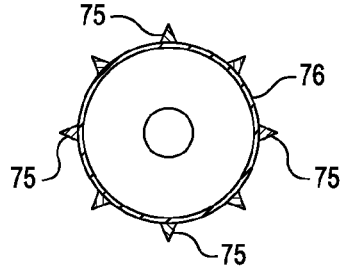

FIG. 10A
(PRIOR ART)
FIG. 10B
(PRIOR ART)
FIG. 10C
(PRIOR ART)
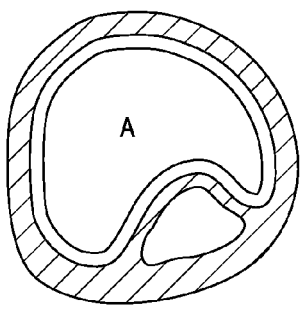
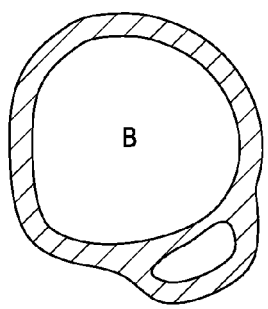
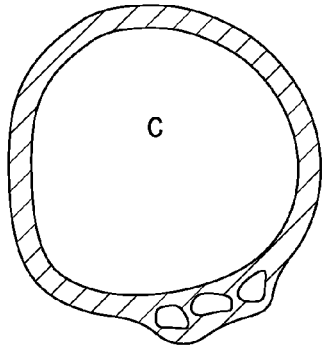
FIG. 11
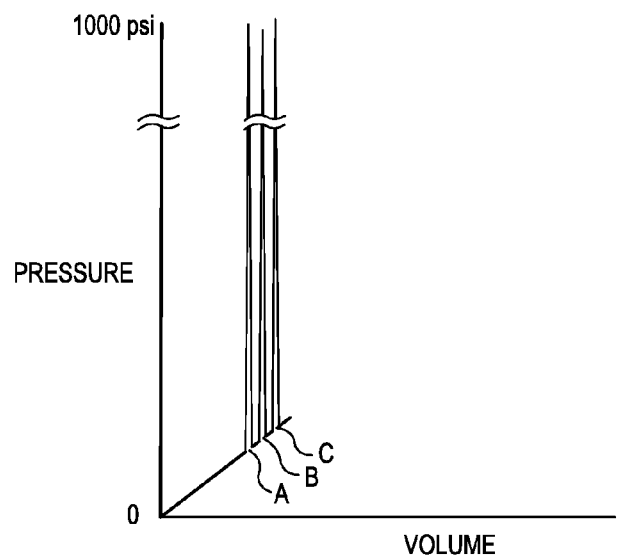
FIG. 11A
FIG. 11B
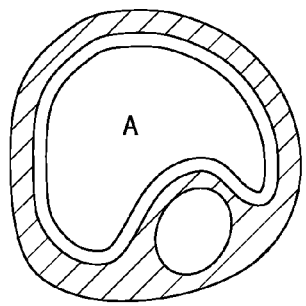
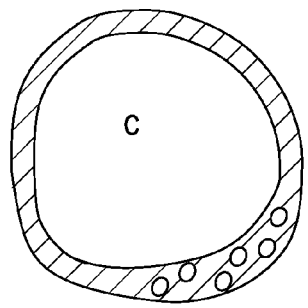

SHOCKWAVE BALLOON CATHETER SYSTEM

PRIORITY CLAIM

The present application claims the benefit of copending U.S. patent application Ser. No. 12/482,995, filed Jun. 11, 2009, which claims the benefit of U.S. Provisional Patent Application Ser. No. 61/061,170, filed Jun. 13, 2008, all of the foregoing applications are incorporated herein by reference in their entireties.

BACKGROUND OF THE INVENTION

The present invention relates to a treatment system for percutaneous coronary angioplasty or peripheral angioplasty in which a dilation catheter is used to cross a lesion in order to dilate the lesion and restore normal blood flow in the artery. It is particularly useful when the lesion is a calcified lesion in the wall of the artery. Calcified lesions require high pressures (sometimes as high as 10-15 or even 30 atmospheres) to break the calcified plaque and push it back into the vessel wall. With such pressures comes trauma to the vessel wall which can contribute to vessel rebound, dissection, thrombus formation, and a high level of restenosis. Non-concentric calcified lesions can result in undue stress to the free wall of the vessel when exposed to high pressures. An angioplasty balloon when inflated to high pressures can have a specific maximum diameter to which it will expand but the opening in the vessel under a concentric lesion will typically be much smaller. As the pressure is increased to open the passage way for blood the balloon will be confined to the size of the open in the calcified lesion (before it is broken open). As the pressure builds a tremendous amount of energy is stored in the balloon until the calcified lesion breaks or cracks. That energy is then released and results in the rapid expansion of the balloon to its maximum dimension and may stress and injure the vessel walls.

SUMMARY OF THE INVENTION

The invention provides a catheter that comprises an elongated carrier, a dilating balloon about the carrier in sealed relation thereto, the balloon being arranged to receive a fluid therein that inflates the balloon, and an arc generator including at least one electrode within the balloon that forms a mechanical shock wave within the balloon.

The at least one electrode may include a single metallic electrode of a pair of metallic electrodes. The electrodes may be radially displaced from each other or longitudinally displaced from each other. The at least one electrode may be formed of stainless steel.

The balloon may be formed of non-compliant material or of compliant material. The dilating balloon may have at least one stress riser carried on its surface.

The catheter may further comprise a sensor that senses reflected energy. The sensor may be distal to the at least one electrode. The sensor may be disposed on the carrier.

The catheter may further comprise a reflector within the dilating balloon that focuses the shock waves. The reflector may form one of the at least one electrodes. The catheter has a center line and the reflector may be arranged to focus the shock waves off of the catheter center line.

The fluid may be saline. The fluid may include an x-ray contrast.

The catheter may further include a lumen for receiving a guide wire. The lumen may be defined by the carrier.

The invention further provides a system comprising a catheter including an elongated carrier, a dilating balloon about the carrier in sealed relation thereto, the balloon being arranged to receive a fluid therein that inflates the balloon, and an arc generator including at least one electrode within the balloon that forms a mechanical shock wave within the balloon. The system further comprises a power source that provides electrical energy to the arc generator.

The power source is preferably arranged to provide pulsed high voltage. The power source may be arranged to provide high voltage pulses having selectable pulse durations, selectable voltage amplitudes, and/or selectable pulse repetition rates.

The system may further comprise an R wave detector that synchronizes the mechanical shock waves with cardiac R waves.

The at least one electrode may include a single metallic electrode of a pair of metallic electrodes. The electrodes may be radially displaced from each other or longitudinally displaced from each other. The at least one electrode may be formed of stainless steel.

The balloon may be formed of non-compliant material or of compliant material. The dilating balloon may have at least one stress riser carried on its surface.

The catheter may further comprise a sensor that senses reflected energy. The sensor may be distal to the at least one electrode. The sensor may be disposed on the carrier.

The catheter may further comprise a reflector within the dilating balloon that focuses the shock waves. The reflector may form one of the at least one electrodes. The catheter has a center line and the reflector may be arranged to focus the shock waves off of the catheter center line.

The fluid may be saline. The fluid may include an x-ray contrast.

The catheter may further include a lumen for receiving a guide wire. The lumen may be defined by the carrier.

The invention further provides a method comprising the step of providing a catheter including an elongated carrier, a dilating balloon about the carrier in sealed relation thereto, the balloon being arranged to receive a fluid therein that inflates the balloon, and an arc generator including at least one electrode within the balloon that forms a mechanical shock wave within the balloon. The method further comprises the steps of inserting the catheter into a body lumen of a patient adjacent an obstruction of the body lumen, admitting fluid into the balloon, and applying high voltage pulses to the arc generator to form a series of mechanical shocks within the balloon.

The method may include the further step of detecting cardiac R waves of the patient's heart, and synchronizing the mechanical shocks with the detected R waves.

The method may further include the step of varying one of the repetition rate, amplitude and duration of the high voltage pulses to vary the intensity of the mechanical shock waves.

The method may include the further step of sensing reflected energy within the catheter.

The method may include the further step of placing a guide wire into the body lumen and guiding the catheter into the body lumen along the guide wire.

The method may include the further step of focusing the mechanical shockwaves. The mechanical shockwaves may be focused away from the catheter center axis.

The method may include the further steps of adding an x-ray contrast to the fluid and visualizing the catheter under fluoroscopy.

BRIEF DESCRIPTION OF THE DRAWINGS

For illustration and not limitation, some of the features of the present invention are set forth in the appended claims. The various embodiments of the invention, together with representative features and advantages thereof, may best be understood by making reference to the following description taken in conjunction with the accompanying drawings, in the several figures of which like reference numerals identify identical elements, and wherein:

FIG. 3A shows voltage pulses that may be obtained with the generator of FIG. 3.

FIG. 4 is a side view of the catheter of FIG. 2 showing an arc between the electrodes and simulations of the shock wave flow.

FIG. 5 is a side view of a dilating catheter with insulated electrodes within the balloon and displaced along the length of the balloon according to another embodiment of the invention.

FIG. 6 is a side view of a dilating catheter with insulated electrodes within the balloon displaced with a single pole in the balloon and a second being the ionic fluid inside the balloon according to a further embodiment of the invention.

FIG. 7 is a side view of a dilating catheter with insulated electrodes within the balloon and studs to reach the calcification according to a still further embodiment of the invention.

FIG. 8 is a side view of a dilating catheter with insulated electrodes within the balloon with raised ribs on the balloon according to still another embodiment of the invention.

FIG. 8A is a front view of the catheter of FIG. 8.

FIG. 10A is a sectional view of a balloon expanding freely within a vessel.

FIG. 10B is a sectional view of a balloon constrained to the point of breaking in a vessel.

FIG. 10C is a sectional view of a balloon after breaking within the vessel.

FIG. 11 is a pressure volume curve showing the various stages in the breaking of a calcified lesion with shock waves according to an embodiment of the invention.

FIG. 11A is a sectional view showing a compliant balloon within a vessel.

FIG. 11B is a sectional view showing pulverized calcification on a vessel wall.

DETAILED DESCRIPTION OF THE INVENTION

Figure 1:
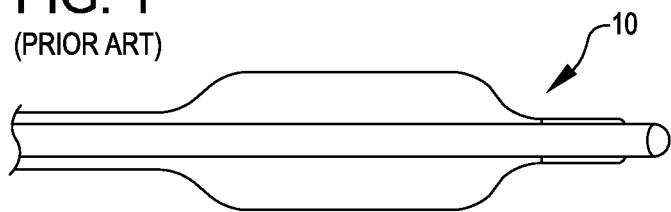
FIG. 1 is a view of the therapeutic end of a typical prior art over-the-wire angioplasty balloon catheter.

FIG. 1 is a view of the therapeutic end of a typical prior art over-the-wire angioplasty balloon catheter 10. Such catheters are usually non-complaint with a fixed maximum dimension when expanded with a fluid such as saline.

Figure 2:
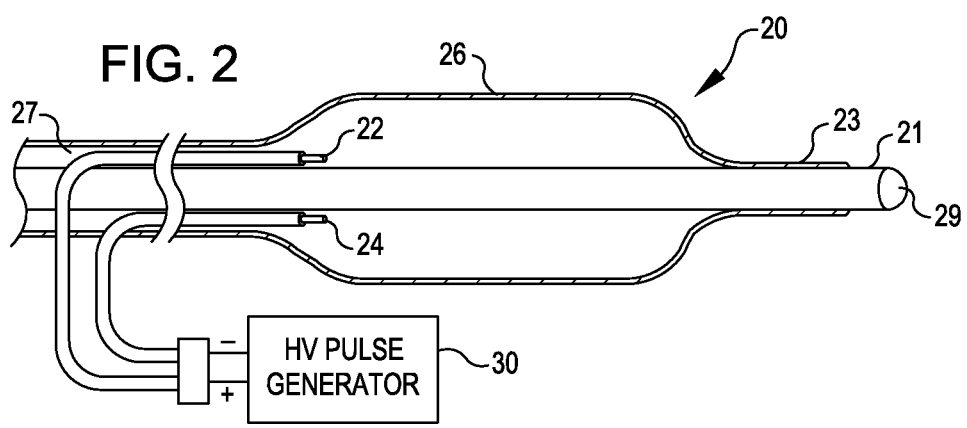
FIG. 2 is a side view of a dilating angioplasty balloon catheter with two electrodes within the balloon attached to a source of high voltage pulses according to one embodiment of the invention.

FIG. 2 is a view of a dilating angioplasty balloon catheter 20 according to an embodiment of the invention. The catheter 20 includes an elongated carrier, such as a hollow sheath 21, and a dilating balloon 26 formed about the sheath 21 in sealed relation thereto at a seal 23. The balloon 26 forms an annular channel 27 about the sheath 21 through which fluid, such as saline, may be admitted into the balloon to inflate the balloon. The channel 27 further permits the balloon 26 to be provided with two electrodes 22 and 24 within the fluid filled balloon 26. The electrodes 22 and 24 are attached to a source of high voltage pulses 30. The electrodes 22 and 24 are formed of metal, such as stainless steel, and are placed a controlled distance apart to allow a reproducible arc for a given voltage and current. The electrical arcs between electrodes 22 and 24 in the fluid are used to generate shock waves in the fluid. The variable high voltage pulse generator 30 is used to deliver a stream of pulses to the electrodes 22 and 24 to create a stream of shock waves within the balloon 26 and within the artery being treated (not shown). The magnitude of the shock waves can be controlled by controlling the magnitude of the pulsed voltage, the current, the duration and repetition rate. The insulating nature of the balloon 26 protects the patient from electrical shocks.

The balloon 26 may be filled with water or saline in order to gently fix the balloon in the walls of the artery in the direct proximity with the calcified lesion. The fluid may also contain an x-ray contrast to permit fluoroscopic viewing of the catheter during use. The carrier 21 includes a lumen 29 through which a guidewire (not shown) may be inserted to guide the catheter into position. Once positioned the physician or operator can start with low energy shock waves and increase the energy as needed to crack the calcified plaque. Such shockwaves will be conducted through the fluid, through the balloon, through the blood and vessel wall to the calcified lesion where the energy will break the hardened plaque without the application of excessive pressure by the balloon on the walls of the artery.

Figure 3:
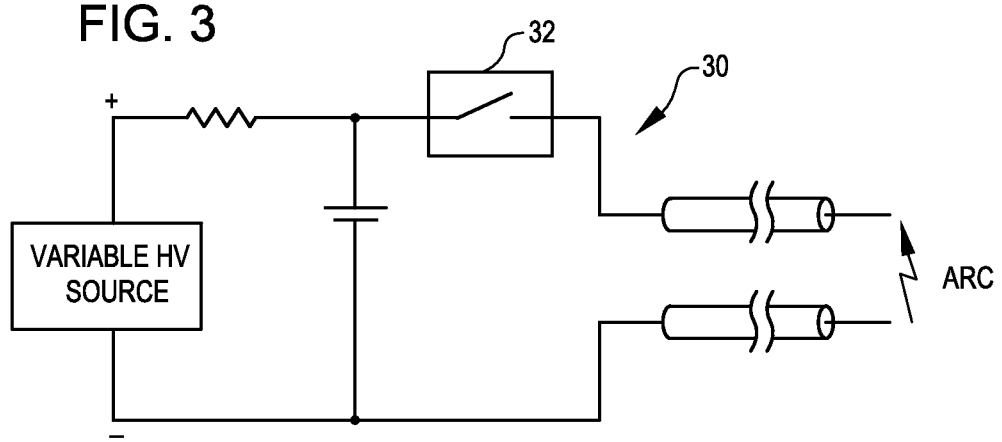
FIG. 3 is a schematic of a high voltage pulse generator.

FIG. 3 is a schematic of the high voltage pulse generator 30. FIG. 3A shows a resulting waveform. The voltage needed will depend on the gap between the electrodes and generally 100 to 3000 volts. The high voltage switch 32 can be set to control the duration of the pulse. The pulse duration will depend on the surface area of the electrodes 22 and 24 and needs to be sufficient to generate a gas bubble at the surface of the electrode causing a plasma arc of electric current to jump the bubble and create a rapidly expanding and collapsing bubble, which creates the mechanical shock wave in the balloon. Such shock waves can be as short as a few microseconds.

FIG. 4 is a cross sectional view of the shockwave catheter 20 showing an arc 25 between the electrodes 22 and 24 and simulations of the shock wave flow 28. The shock wave 28 will radiate out from the electrodes 22 and 24 in all directions and will travel through the balloon 26 to the vessel where it will break the calcified lesion into smaller pieces.

FIG. 5 shows another dilating catheter 40. It has insulated electrodes 42 and 44 within the balloon 46 displaced along the length of the balloon 46.

FIG. 6 shows a dilating catheter 50 with an insulated electrode 52 within the balloon 56. The electrode is a single electrode pole in the balloon, a second pole being the ionic fluid 54 inside the balloon. This unipolar configuration uses the ionic fluid as the other electrical pole and permits a smaller balloon and catheter design for low profile balloons. The ionic fluid is connected electrically to the HV pulse generator 30.

FIG. 7 is another dilating 60 catheter with electrodes 62 and 64 within the balloon 66 and studs 65 to reach the calcification. The studs 65 form mechanical stress risers on the balloon surface 67 and are designed to mechanically conduct the shock wave through the intimal layer of tissue of the vessel and deliver it directly to the calcified lesion.

FIG. 8 is another dilating catheter 70 with electrodes 72 and 74 within the balloon 76 and with raised ribs 75 on the surface 77 of the balloon 76. The raised ribs 75 (best seen in FIG. 8A) form stress risers that will focus the shockwave energy to linear regions of the calcified plaque.

Figure 9:
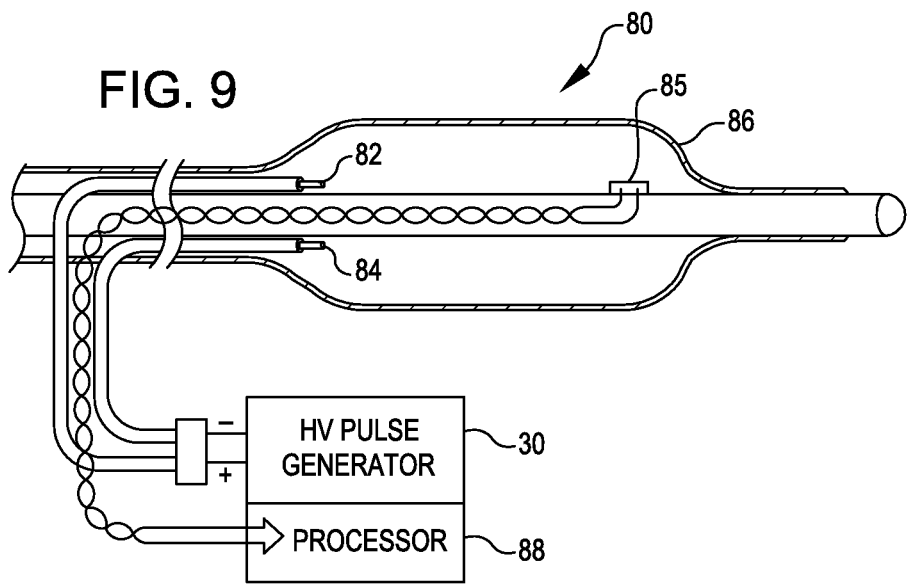
FIG. 9 is a side view of a dilating catheter with insulated electrodes within the balloon and a sensor to detect reflected signals according to a further embodiment of the invention.

FIG. 9 is a further dilating catheter 80 with electrodes 82 and 84 within the balloon 86. The catheter 80 further includes a sensor 85 to detect reflected signals. Reflected signals from the calcified plaque can be processed by a processor 88 to determine quality of the calcification and quality of pulverization of the lesion.

Figure 10:
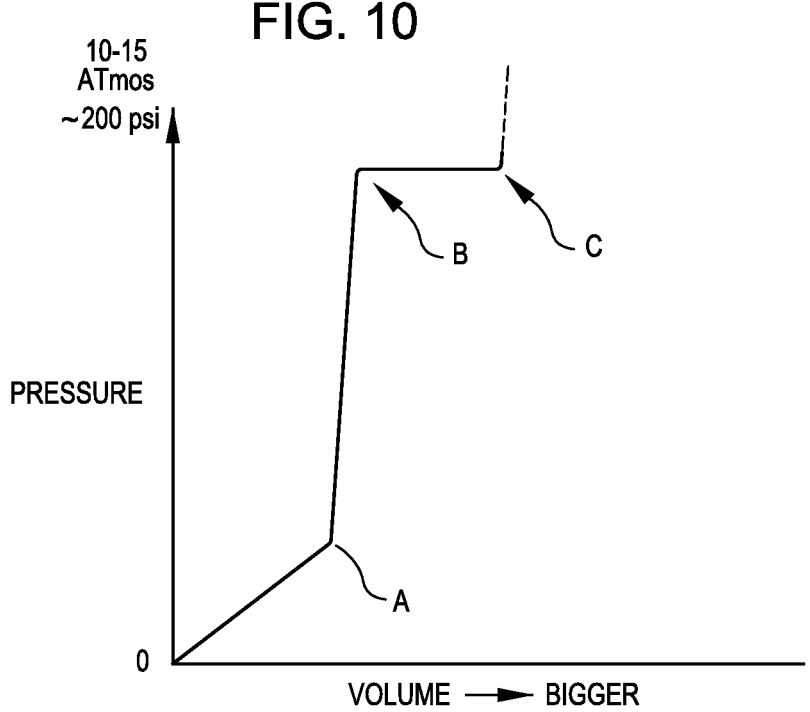
FIG. 10 is a pressure volume curve of a prior art balloon breaking a calcified lesion.

FIG. 10 is a pressure volume curve of a prior art balloon breaking a calcified lesion. FIG. 10B shows the build up of energy within the balloon (region A to B) and FIG. 10C shows the release of the energy (region B to C) when the calcification breaks. At region C the artery is expanded to the maximum dimension of the balloon. Such a dimension can lead to injury to the vessel walls. FIG. 10A shows the initial inflation of the balloon.

FIG. 11 is a pressure volume curve showing the various stages in the breaking of a calcified lesion with shock waves according to the embodiment. The balloon is expanded with a saline fluid and can be expanded to fit snugly to the vessel wall (Region A) (FIG. 11A) but this is not a requirement. As the High Voltage pulses generate shock waves (Region B and C) extremely high pressures, extremely short in duration will chip away the calcified lesion slowly and controllably expanding the opening in the vessel to allow blood to flow un-obstructed (FIG. 11B).

Figure 12:
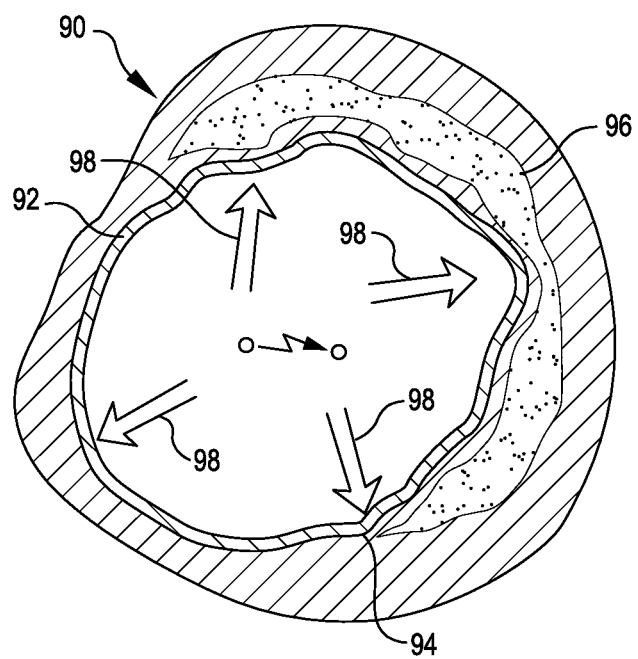
FIG. 12 illustrates shock waves delivered through the balloon wall and endothelium to a calcified lesion.

FIG. 12 shows, in a cutaway view, shock waves 98 delivered in all directions through the wall 92 of a saline filled balloon 90 and intima 94 to a calcified lesion 96. The shock waves 98 pulverize the lesion 96. The balloon wall 92 may be formed of non-compliant or compliant material to contact the intima 94.

Figure 13:
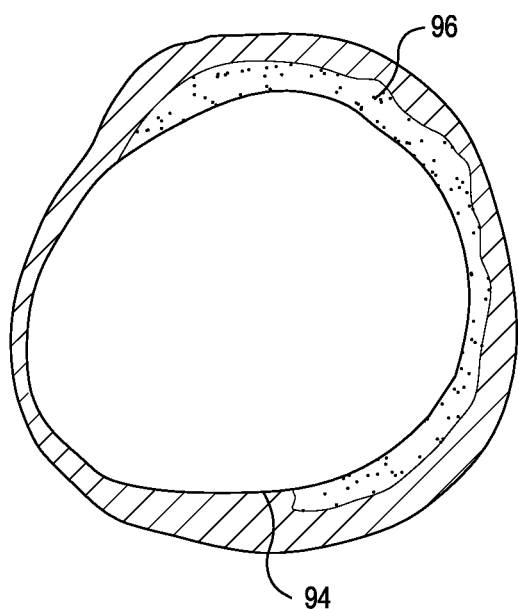
FIG. 13 shows calcified plaque pulverized and smooth a endothelium restored by the expanded balloon after pulverization.

FIG. 13 shows calcified plaque 96 pulverized by the shock waves. The intima 94 is smoothed and restored after the expanded balloon (not shown) has pulverized and reshaped the plaque into the vessel wall.

Figure 14:
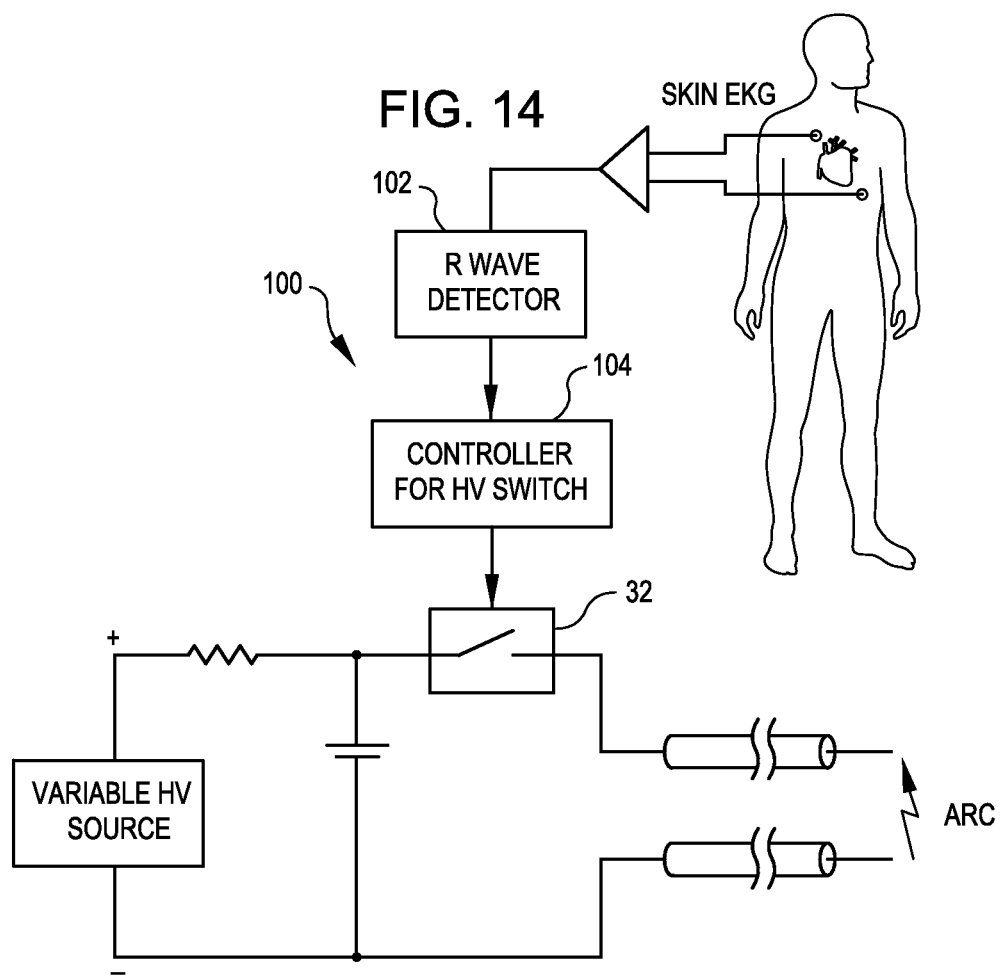
FIG. 14 is a schematic of a circuit that uses a surface EKG to synchronize the shock wave to the "R" wave for treating vessels near the heart.

FIG. 14 is a schematic of a circuit 100 that uses the generator circuit 30 of FIG. 3 and a surface EKG 102 to synchronize the shock wave to the "R" wave for treating vessels near the heart. The circuit 100 includes an R-wave detector 102 and a controller 104 to control the high voltage switch 32. Mechanical shocks can stimulate heart muscle and could lead to an arrhythmia. While it is unlikely that shockwaves of such short duration as contemplated herein would stimulate the heart, by synchronizing the pulses (or bursts of pulses) with the R-wave, an additional degree of safety is provided when used on vessels of the heart or near the heart. While the balloon in the current drawings will provide an electrical isolation of the patient from the current, a device could be made in a non-balloon or non-isolated manner using blood as the fluid. In such a device, synchronization to the R-wave would significantly improve the safety against unwanted arrhythmias.

Figure 15:
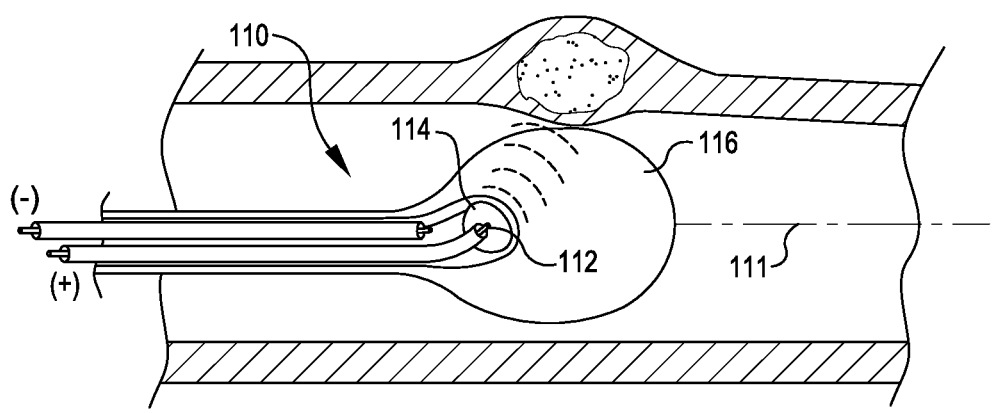
FIG. 15 is a side view, partly cut away, of a dilating catheter with a parabolic reflector acting as one electrode and provides a focused shock wave inside a fluid filled compliant balloon.

FIG. 15 shows a still further dilation catheter 110 wherein a shock wave is focused with a parabolic reflector 114 acting as one electrode inside a fluid filled compliant balloon 116. The other electrode 112 is located at the coaxial center of the reflector 114. By using the reflector as one electrode, the shock wave can be focused and therefore pointed at an angle (45 degrees, for example) off the center line 111 of the catheter artery. In this configuration, the other electrode 112 will be designed to be at the coaxial center of the reflector and designed to arc to the reflector 114 through the fluid. The catheter can be rotated if needed to break hard plaque as it rotates and delivers shockwaves.

While particular embodiments of the present invention have been shown and described, modifications may be made. For example, instead of manual actuation and spring loaded return of the valves used herein, constructions are possible which perform in a reversed manner by being spring actuated and manually returned. It is therefore intended in the appended claims to cover all such changes and modifications which fall within the true spirit and scope of the invention as defined by those claims.

What is claimed is:

1. A method for cracking calcified lesions in the wall of a blood vessel of a patient comprising:
    providing a catheter including an elongated carrier, an angioplasty balloon at one end of the carrier in sealed relation thereto, the carrier defining a guide wire lumen extending through the balloon, the balloon having an outer surface and being arranged to receive a fluid therein that inflates the balloon, and an arc generator including a pair of electrodes located between the guide wire lumen and the outer surface of the balloon;
    inserting the catheter into the blood vessel of a patient on a guide wire adjacent to a calcified lesion;
    admitting fluid into the balloon after inserting the catheter into the blood vessel of a patient; and
    applying high voltage pulses to the arc generator to form a series of mechanical shock waves originating between the guide wire lumen and the outer surface of the balloon with the shock waves being conducted through the balloon to crack the calcified lesions while the balloon remains intact.

2. The method of claim 1, including the further step of detecting cardiac R waves of the patient's heart, and synchronizing the mechanical shock waves with the detected R waves.

3. The method of claim 1, including the further step of varying one of a repetition rate, amplitude and duration of the high voltage pulses to vary an intensity of the mechanical shock waves.

4. The method of claim 1, including the further step of placing the guide wire into the blood vessel and guiding the catheter into the blood vessel along the guide wire.

5. The method of claim 1 including the further step of focusing the mechanical shockwaves.

6. The method of claim 1 wherein the arc generator is arranged for focusing the shockwaves in a direction off of a center line of the catheter and wherein the method further includes the step of rotating the arc generator as the high voltage pulses are applied to the pair of electrodes.

7. The method of claim 6, wherein the rotating step includes rotating the pair of electrodes.

8. The method of claim 7, wherein the rotating step includes rotating the catheter.

* * * * *